United States Patent
Dal Molin

(10) Patent No.: US 6,725,091 B2
(45) Date of Patent: Apr. 20, 2004

(54) MEASURING A TRANS-SEPTUM BIO-IMPEDANCE IN AN ACTIVE IMPLANTABLE MEDICAL DEVICE, IN A PARTICULAR PACEMAKER, DEFIBRILLATOR AND/OR CADIOVERTOR AND/OR MULTISITE DEVICE

(75) Inventor: Renzo Dal Molin, Chatillon (FR)

(73) Assignee: ELA Medical S.A., Montrouge (FR)

( * ) Notice: Subject to any disclaimer, the term of this patent is extended or adjusted under 35 U.S.C. 154(b) by 471 days.

(21) Appl. No.: 09/808,740

(22) Filed: Mar. 14, 2001

(65) Prior Publication Data

US 2001/0034540 A1 Oct. 25, 2001

(30) Foreign Application Priority Data

Mar. 14, 2000 (FR) .............................................. 00 03243

(51) Int. Cl.$^7$ ................................................ A61N 1/368
(52) U.S. Cl. .............................. 607/2; 607/20; 607/28; 607/122; 607/8; 600/508; 600/547
(58) Field of Search ................................. 607/2, 20, 28, 607/122, 123, 4, 5, 6, 8, 17, 18, 9, 21, 22, 23, 24, 25, 26, 27, 29; 600/508, 547, 510, 517

(56) References Cited

U.S. PATENT DOCUMENTS

| | | | |
|---|---|---|---|
| 5,154,171 A | | 10/1992 | Chirife ................. 128/419 PG |
| 5,388,586 A | * | 2/1995 | Lee et al. ................... 600/517 |
| 5,501,702 A | | 3/1996 | Plicchi et al. ................. 607/20 |
| 5,522,860 A | | 6/1996 | Molin et al. .................. 607/20 |
| 5,649,965 A | * | 7/1997 | Pons et al. ...................... 607/2 |
| 5,697,960 A | * | 12/1997 | Molin et al. .................... 607/2 |
| 5,702,426 A | * | 12/1997 | Pons et al. ...................... 607/27 |
| 5,902,325 A | | 5/1999 | Condie et al. ................ 607/28 |
| 5,995,870 A | * | 11/1999 | Cazeau et al. ................. 607/9 |
| 6,539,261 B2 | * | 3/2003 | Dal Molin .................... 607/20 |
| 6,556,866 B2 | * | 4/2003 | Dal Molin et al. ............. 607/9 |
| 6,591,131 B2 | * | 7/2003 | Dal-Molin .................. 600/510 |
| 6,604,002 B2 | * | 8/2003 | Molin ......................... 607/28 |

FOREIGN PATENT DOCUMENTS

| | | | |
|---|---|---|---|
| EP | 0 925 806 A1 | 6/1999 | .......... A61N/1/368 |
| WO | 99/30777 | 6/1999 | .......... A61N/1/368 |

* cited by examiner

Primary Examiner—Henry Bennett
Assistant Examiner—Fadi H. Dahbour
(74) Attorney, Agent, or Firm—Orrick Herrington & Sutcliffe, LLP

(57) ABSTRACT

An active implantable medical device, in particular a pacemaker, cardioverter, defibrillator and/or a multisite device having circuits for measuring a trans-septal bio-impedance. This device is used with electrodes placed in a plurality of distinct respective sites comprising at least one left ventricular site and one right atrial site. These electrodes are connected to a collection circuit for collecting cardiac signals, in particular to detect a potential of depolarization, and to a stimulation circuit, to apply stimulation pulses to at least some of the aforementioned sites. The device evaluates the cardiac flow by obtaining an intracardiac measurement of the bio-impedance, more particularly measuring the trans-septum impedance bio-between the left ventricle and the right atrium, by injection of a current (16) between an atrial site (RA−) and a ventricular site (LV−), and collection of a differential potential (20) between an atrial site (RA+) and a ventricular site (LV−).

13 Claims, 1 Drawing Sheet

MEASURING A TRANS-SEPTUM BIO-IMPEDANCE IN AN ACTIVE IMPLANTABLE MEDICAL DEVICE, IN A PARTICULAR PACEMAKER, DEFIBRILLATOR AND/OR CADIOVERTOR AND/OR MULTISITE DEVICE

FIELD OF THE INVENTION

The present invention relates to "active implantable medical devices" as such devices are defined by the Jun. 20, 1990 directive 90/385/CEE of the Council of the European Communities, more particularly to pacemaker, defibrillator and/or cardiovertor devices that are able to deliver to the heart stimulation pulses of low energy for the treatment of heartbeat rate disorders. The invention is more particularly directed to the prostheses known as "multisite", in which respective electrodes are placed in a plurality of distinct respective cardiac sites comprising at least one ventricular site and one atrial site. This prosthesis can be of the "triple chamber" (right atrial stimulation and double ventricular stimulation) or "quadruple chamber" (double atrial stimulation and double ventricular stimulation) type.

BACKGROUND OF THE INVENTION

The control of stimulation implies making an adjustment of various control parameters, such as the stimulation frequency, the atrio-ventricular delay (AVD), or the inter-ventricular delay in the case of a biventricular stimulation. These various parameters are typically adjusted according to signals delivered by sensors, for example, a minute ventilation (MV) sensor. The minute ventilation is a factor which is representative of the instantaneous metabolic needs of the patient. This factor, in a known manner, is evaluated by measurement of a trans-pulmonary bioimpedance, i.e., between the heart and the case of pacemaker, where the case is located in the top of the thorax.

Another factor which is desirable to know is the cardiac flow. It can be interesting, particularly with a multisite pacemaker, to obtain an indication of this flow and thus of the fraction of ejection. The fraction of ejection is the hemodynamic reference parameter used to optimize stimulation on the various cardiac sites. The cardiac flow can be evaluated by measurement of the intracardiac pressure, for example, as proposed in the published application WO-A-99/34863 (Pacesetter AB), but at an expense of requiring a specific probe incorporating a piezoelectric sensor and particular associated electronics to condition the signals resulting from this sensor, to convert them and transmit them to the microprocessor of the pacemaker for processing and use.

Another parameter correlated with the cardiac flow is the transvalvular impedance, a parameter that is generally measured on the right heart, for example, as proposed in U.S. Pat. No. 5,154,171 (Chirife). This document proposes to take the bio-impedance measurement by injecting a current pulse between a ventricular site and an atrial site, and collecting a differential potential between these same two sites. In practice, however, it is noted that this configuration (a bipolar configuration of two electrodes) of injection/collection appears sensitive to the movement of the probes containing the electrodes, and does not allow a reliable and precise measurement of the impedance and of the fraction of ejection.

OBJECTS AND SUMMARY OF THE INVENTION

It is, therefore, an object of the present invention to overcome the foregoing disadvantages by proposing an improved configuration for measuring the intracardiac impedance and procuring a more reliable and more precise measure of the fraction of ejection, in particular for use in controlling the inter-ventricular delay (in the case of a biventricular stimulation), the stimulation frequency, and/or the atrio-ventricular delay.

Broadly, the present invention relates to a medical device of the known general type, for example, a device according to U.S. Pat. No. 5,154,171 mentioned above, i.e., in which electrodes are to be placed in a plurality of distinct respective sites comprising at least one left ventricular site and one right atrial site, or at least one right ventricular site and one left atrial site. These electrodes are to be connected to a collection (detection) circuit, able to collect (detect) cardiac signals including a potential of depolarization, and to a stimulation circuit, able to apply stimulation pulses to at least certain of the aforesaid sites. The stimulation circuit and the collection circuit typically are located inside the case of the device. The device of the present invention also comprises a means for evaluating the cardiac flow by measurement of the intracardiac bio-impedance. It should be understood that the term "site" is used synonymously with the term cavity.

In a characteristic manner of the invention, the means for evaluating the cardiac flow further comprises means for measuring a trans-septum bio-impedance, which measurement is made either between the left ventricle and right atrium, or between the right ventricle and the left atrium. The trans-septum bio-impedance measuring means operates by injecting a current between an atrial site and a ventricular site, and collecting a differential potential between an atrial site and a ventricular site.

In a first embodiment, the means for measuring the trans-septum impedance operates the aforementioned current injection between a common ventricular site and a first atrial injection site, and operates the aforementioned collection of the differential potential between the aforementioned common ventricular site and a second atrial collection site.

In another embodiment, the means for measuring the trans-septum bio-impedance operates the aforementioned current injection between a common atrial site and a first ventricular injection site, and operates the aforementioned collection of the differential potential between the aforementioned common atrial site and a second ventricular collection site.

In the foregoing embodiments, in the cavity of the common site, preferably the same electrode is used for the injection and the collection, and in the cavity of the non-common sites, preferably different electrodes in the same cavity are used for the injection and collection, which different electrodes are more preferably disposed on the same lead.

Preferably, the device also includes means for varying the stimulation pulse frequency is applied, means for varying the atrio-ventricular delay applied, and/or means for varying the inter-ventricular delay applied, with respect to the right and left ventricles, all of these means operating in response to the measured trans-septum bio-impedance to vary the parameter in a direction towards an improvement of the cardiac flow.

In addition, the device optionally includes means for detecting ventricular arrhythmias and means for discriminating between, on the one hand, patient effort (i.e., activity above a rest level of activity) accompanied by an elevated heart rate, and, on the other hand, disorders of the heart rate accompanied by a fall of the cardiac flow as detected by the means for measuring the trans-septum bio-impedance.

BRIEF DESCRIPTION OF THE DRAWINGS

Other features, characteristics, and advantages of the present invention will appear to a person of ordinary skill in the art in view of the following detailed description of preferred embodiments of the present invention, made with reference to the annexed drawings, in which the same numerical and word references indicate similar elements, and in which.

DETAILED DESCRIPTION OF THE DRAWINGS

Figure 1:
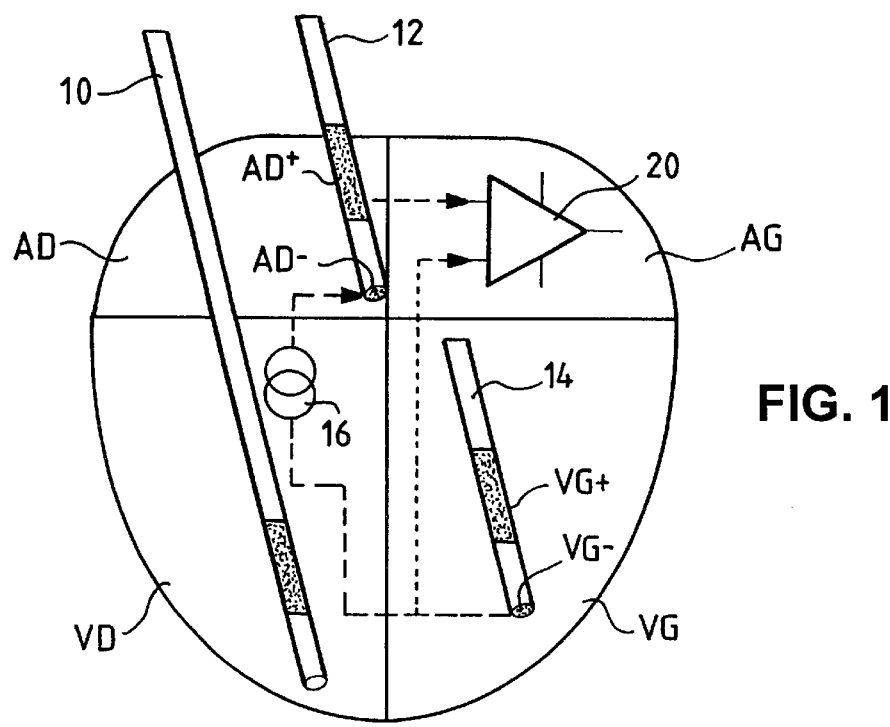
FIG. 1 illustrates a configuration for the measurement of the atrio-ventricular trans-septum bio-impedance in accordance with a preferred embodiment of the present invention.

FIG. 1 schematically represents a cardiac muscle with its four cavities: right atrium RA, left atrium LA, right ventricle RV and left ventricle LV. A ventricular probe 10 is shown introduced into right ventricle RV (although it should be understood that this probe 10 does not play any role in the particular implementation of the present invention).

An atrial probe 12 is introduced into right atrium RA, having an annular proximal electrode RA+ and a distal tip electrode RA−. It also is envisaged to insert a probe 14 on left ventricle LV, having an annular proximal electrode LV+ and a distal tip electrode LV−.

The electrodes of these probes are connected to a case including various detection, stimulation and control circuits, for example, a case of a multisite pacemaker such as that described in the published application EP-A-0 925 806 (corresponding to a pending and commonly assigned U.S. patent application Ser. No. 09/218,678 (ELA Médical), the disclosure of which is incorporated herein by reference), to which one can refer for additional details.

In accordance with the present invention, an oblique measurement of the trans-septum bio-impedance is obtained, i.e., a measurement between the right atrium RA and left ventricle LV. This measurement is carried out by an injection of a current pulse (schematized by the current generator 16) between two electrodes in the two sites, and collection of a differential potential (schematized by the operational amplifier 20) between two electrodes in the two sites.

The injection and the collection of the signals at these various points can be operated by means of a circuit such as the one described in U.S. Pat. No. 5,154,171 mentioned above. The technique described is a measurement of the trans-valvular impedance (made between the right atrium and the right ventricle). Alternately the injection and collection of the signals can be obtained by use of a circuit such as those commonly used for measurement of the minute ventilation (MV) on the existing rate responsive cardiac control devices.

To carry out the oblique measurement of a trans-septum bio-impedance according to the invention, the points of current injection and signal collection are modified in the manner that described below, as compared to the known configurations. In addition, the signal collection is operated at different frequency bands: relative to the frequency used for the measurement of MV, a higher frequency is used for the measurement of trans-septum bio-impedance. The modification of the frequency band can result, for example, from a displacement of the cut-off points of a frequency band pass filter, which modification is particularly easy to carry out by software if the filtering technique used is a digital filtering.

It is thus possible, and particularly advantageous, to use the preexisting apparatus and procedures for measuring the minute ventilation of a device in the traditional manner, and to recover the measurement signal that is collected before the stage of the MV filtering. Thus, the present invention allows for a realization of the aforementioned improvement without a large added cost.

The current injected for the measurement of the impedance according to the invention is, for example, a current of 40 $\mu$A, delivered in the form of a pulse of 5 $\mu$S width. Other values could of course be used.

The measurement configuration (injection/collection) according to the invention is preferably a tripolar configuration, with one point common to the injection and the collection. A currently preferred configuration, as illustrated in FIG. 1, is:

current injection between LV− and RA−, and signal collection between LV− and RA+.

In other words, the common point, i.e., the measurement reference, is the ventricular distal tip electrode LV−.

Figure 2:
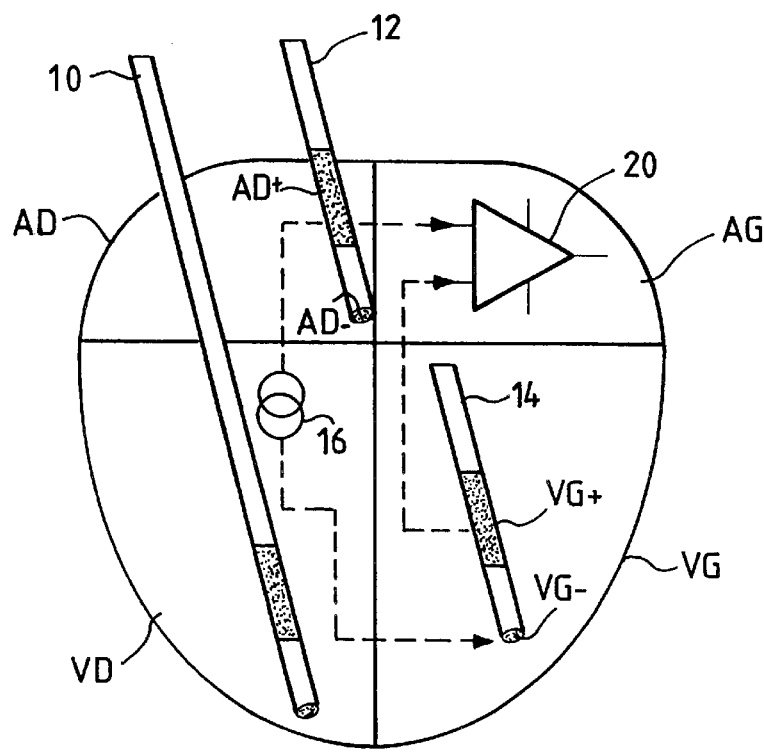
FIG. 2 illustrates an alternative of the embodiment of FIG. 1.

In the alternative embodiment of FIG. 2, the common point is selected to be the atrial proximal electrode RA+, i.e., the configuration is:

current injection between RA+ and LV−, signal collection between RA+ and LV+

In addition, for all the foregoing configurations, it is possible to reverse the role of the proximal electrodes (+) and the distal tip electrodes (−), as well as to use distal electrodes which are not tip electrodes.

This trans-septum bio-impedance measurement makes it possible to have a signal correlated to the variations of the left ventricular volume, without needing to measure the variations of the right ventricular volume.

It is all the more advantageous to have directly information on the hemodynamic behavior of the left ventricle, which is the prevailing ventricle, and which produces the blood pressure (the right ventricle reflects the blood pressure only in an indirect and temporally shifted way as compared to the left ventricle). It is possible, however, if one wishes to reverse the configuration for operating between right ventricle and left atrium, to thus obtain a measurement of the flow in the right heart (which is, in average value, equal to the flow of the left heart).

The signal collected can be used to control the stimulation frequency and/or the atrio-ventricular delay and/or the interventricular delay in the case of a biventricular stimulation. The to adjustment of these various parameters is done of course in the direction that will produce the maximum cardiac flow.

The device also can optionally include means to detect ventricular arrhythmias by providing information relating to the patient's hemodynamic condition. This makes it possible to discriminate between, on the one hand, a patient effort accompanied by a detected high cardiac frequency and, on the other hand, a disorder of the cardiac rate accompanied by a fall of the cardiac flow.

One skilled in the art will appreciate that the present invention can be practiced by other than the described embodiments, which are presented for purposes of illustration and not of limitation.

I claim:

1. An active implantable medical device, in particular a pacemaker, defibrillator and/or cardiovertor and/or a multisite device, including a cardiac signal collection circuit, to detect a potential of depolarization, and a stimulation circuit, to apply stimulation pulses, said circuits being connectable to at least two electrodes placed in a plurality of distinct respective sites comprising at least one left ventricular site and one right atrial site, or at least one right ventricular site and one left atrial site, said device further comprising means for measuring an intracardiac measurement of bio-impedance and evaluating a cardiac flow based on said impedance, said device being characterized in that the means for evaluating the cardiac flow further comprises means for measuring a trans-septum bio-impedance between one of the left ventricle and the right atrium, and the right ventricle and the left atrium, respectively, by injection of a current between an atrial site and a ventricular site and collection of a differential potential between an atrial site and a ventricular site.

2. The device of claim 1, wherein the means for measuring the trans-septum bio-impedance is able to operate said current injection between a common ventricular site and a first atrial injection site, and to operate said collection of the differential potential between said common ventricular site and a second atrial collection site.

3. The device of claim 2, wherein the common ventricular site is the left ventricular cavity and the first and second atrial sites are the right atrial cavity.

4. The device of claim 1, wherein the means for measuring the trans-septum bio-impedance is able to operate said current injection between a common atrial site and a first ventricular injection site, and operate the aforementioned collection of the differential potential between said common atrial site and a second ventricular collection site.

5. The device claim 4, wherein the common atrial site is the left atrial cavity and the first and second ventricular sites are the right ventricular cavity.

6. The device of claim 1, further comprising means for varying a stimulation pulse frequency in response to the measured trans-septum bio-impedance in a direction of an improvement of the cardiac flow.

7. The device of claim 1, further comprising means for varying an atrio-ventricular delay in an application of the stimulation pulses, in response to the trans-septum bio-impedance measured in a direction of an improvement of the cardiac flow.

8. The device of claim 1, further comprising means for varying an inter-ventricular delay in an application of respective stimulation pulses of the right and left ventricles, in response to the measured trans-septum bio-impedance, in a direction of an improvement of the cardiac flow.

9. The device of claim 1, further comprising means for detecting a ventricular arrhythmia and for discriminating between a patient effort accompanied by an increase in the heart rate and a heartbeat rate disorder accompanied by a fall of the cardiac flow detected by the means for measuring the trans-septum bio-impedance.

10. The device of claim 1, wherein the means for measuring the trans-septum bio-impedance is able to operate said current injection between a common point in said ventricular site and an injection point in said atrial site, and to operate said collection of the differential potential between said common point and a collection point in said atrial site.

11. The device of claim 10, wherein the ventricular site is the left ventricular cavity and the atrial site is the right atrial cavity.

12. The device of claim 1, wherein the means for measuring the trans-septum bio-impedance is able to operate said current injection between a common point in said atrial site and an injection point in said ventricular site, and operate the aforementioned collection of the differential potential between said common point and a collection point in said ventricular site.

13. The device claim 12, wherein the atrial site is the left atrial cavity and the ventricular site is the right ventricular cavity.

* * * * *

UNITED STATES PATENT AND TRADEMARK OFFICE
CERTIFICATE OF CORRECTION

| | | |
|---|---|---|
| PATENT NO. | : 6,725,091 B2 | Page 1 of 1 |
| APPLICATION NO. | : 09/808740 | |
| DATED | : April 20, 2004 | |
| INVENTOR(S) | : Renzo Dal Molin | |

It is certified that error appears in the above-identified patent and that said Letters Patent is hereby corrected as shown below:

On the Title Pg, Item (57)

IN THE ABSTRACT

Line 13–14, after "measuring the trans-septum" and before "the left," "impedance bio-between" should be changed to --bio-impedance between--.

IN THE SPECIFICATION

Column 1, line 52, "right heart" should be changed to --right heart chamber--.

Column 2, line 54, after "stimulation pulse frequency" and before "applied," delete "is".

Column 4, line 48, after "The" and before "adjustment," delete "to".

IN THE CLAIMS

Claim 5, line 2, "The device claim" should be changed to --The device of claim--.

Claim 13, line 1, "The device claim" should be changed to --The device of claim--.

Signed and Sealed this

Eleventh Day of October, 2011

David J. Kappos
*Director of the United States Patent and Trademark Office*

UNITED STATES PATENT AND TRADEMARK OFFICE
CERTIFICATE OF CORRECTION

PATENT NO. : 6,725,091 B2
APPLICATION NO. : 09/808740
DATED : April 20, 2004
INVENTOR(S) : Renzo Dal Molin Page 1 of 1

It is certified that error appears in the above-identified patent and that said Letters Patent is hereby corrected as shown below:

On the Title Pg, Item (57)

IN THE ABSTRACT

Line 13–14, after "measuring the trans-septum" and before "the left," "impedance bio-between" should be changed to --bio-impedance between--.

IN THE SPECIFICATION

Column 1, line 52, "right heart" should be changed to --right heart chamber--.

Column 2, line 54, after "stimulation pulse frequency" and before "applied," delete "is".

Column 4, line 48, after "The" and before "adjustment," delete "to".

IN THE CLAIMS

Column 5, line 30 (Claim 5, line 1) "The device claim" should be changed to --The device of claim--.

Column 6, line 34 (Claim 13 line 1) "The device claim" should be changed to --The device of claim--.

This certificate supersedes the Certificate of Correction issued October 11, 2011.

Signed and Sealed this
Eighth Day of November, 2011

David J. Kappos
*Director of the United States Patent and Trademark Office*